United States Patent
Sarvazyan

(10) Patent No.: US 7,955,278 B1
(45) Date of Patent: Jun. 7, 2011

(54) ASPIRATION METHODS AND DEVICES FOR ASSESSMENT OF VISCOELASTIC PROPERTIES OF SOFT TISSUES

(75) Inventor: Armen P. Sarvazyan, Lambertville, NJ (US)

(73) Assignee: Artann Laboratories Inc., West Trenton, NJ (US)

( * ) Notice: Subject to any disclaimer, the term of this patent is extended or adjusted under 35 U.S.C. 154(b) by 9 days.

(21) Appl. No.: 12/627,068

(22) Filed: Nov. 30, 2009

(51) Int. Cl.
*A61B 5/103* (2006.01)
*A61B 5/117* (2006.01)

(52) U.S. Cl. .......... 600/587; 600/557; 600/561

(58) Field of Classification Search .......... 600/587, 600/557, 561
See application file for complete search history.

(56) References Cited

U.S. PATENT DOCUMENTS

| | | | |
|---|---|---|---|
| 4,365,638 A | 12/1982 | Leveque | |
| 4,976,272 A * | 12/1990 | Bazin et al. | 600/587 |
| 5,054,502 A * | 10/1991 | Courage | 600/587 |
| 5,278,776 A | 1/1994 | Fisher | |
| 5,379,235 A * | 1/1995 | Fisher et al. | 600/587 |
| 5,706,815 A * | 1/1998 | Sarvazyan et al. | 600/438 |
| 7,556,605 B2 * | 7/2009 | Qu et al. | 600/587 |
| 2008/0234607 A1 * | 9/2008 | Hunter-Jones et al. | 600/587 |

FOREIGN PATENT DOCUMENTS

WO 03/105689 12/2003

OTHER PUBLICATIONS

Cutometer MPA 580 technical brochure, downloaded from http://www.dutechscientific.com/download/MPA580.pdf on Feb. 18, 2011.

* cited by examiner

*Primary Examiner* — Jeffrey G Hoekstra
*Assistant Examiner* — Charles Becker
(74) *Attorney, Agent, or Firm* — Boris Leschinsky

(57) ABSTRACT

Methods for assessing viscoelastic properties of soft tissues are based on detecting an inflection point on a pressure-time plot when air is aspirated from a cavity placed over the tissue sample. A small diameter tube through which air aspiration is conducted is ultimately closed off by tissue being drawn into the cavity causing an abrupt change in pressure slope. First or second derivatives of the pressure-time plot can be used to detect the inflection point. Repeating the test with a different aspiration rates or after a predetermined relaxation time allows determining tissue viscosity and tissue creep in addition to tissue elasticity expressed as Young's modulus.

6 Claims, 13 Drawing Sheets

ASPIRATION METHODS AND DEVICES FOR ASSESSMENT OF VISCOELASTIC PROPERTIES OF SOFT TISSUES

BACKGROUND OF INVENTION

The invention relates to methods and devices for assessing viscoelastic properties of soft tissues. In particular, the invention relates to using aspiration methods to detect elasticity, viscosity, creep and other properties of accessible living tissues such as skin, cervix, vaginal wall, etc.

Mechanical properties of skin (e.g., elasticity of skin) may change due to disease, stress, or dehydration. When the body becomes dehydrated as a result of diseases such as those that cause diarrhea or reduced liquid intake such as famine or marathon running, the skin becomes "doughy" and does not snap back when pinched. In a test for dehydration called the "pinch test" or "turgor test," the skin is grasped and pulled up in a pinch-like manner and then released. Healthy skin will quickly snap back to its undeformed state, whereas dehydrated skin returns to its undeformed state slowly. Such conventional test is subjective and inaccurate. Objective determination of skin elasticity is important for detecting a state of dehydration as well as diagnosis of other pathological conditions.

Characterizing viscoelastic properties of other human soft tissues is clinically important as well. One such tissue is female uterine cervix. The occurrence of cervical ripening before 34 weeks of gestation leading to preterm delivery represents a serious medical problem. Preterm delivery is a major cause of perinatal morbidity and mortality. About 12.5 percent of babies (more than half a million a year) in the United States are born prematurely. For reasons that doctors do not fully understand, the rate of premature birth has increased by more than 30 percent since 1981. Premature babies are at increased risk for newborn health complications, as well as lasting disabilities, such as mental retardation, cerebral palsy, lung and gastrointestinal problems, vision and hearing loss, and even death.

The uterine cervix has to provide mechanical resistance to ensure a normal development of the fetus. Cervical softening occurs progressively in the last one-third of pregnancy. The process of cervical ripening, consisting of softening of the connective tissue components, is not easily identifiable with present methods. Objective quantitative assessment of cervical ripening will allow dispensing of therapy for preterm labor. Specific defects in cervical ripening will then be diagnosed and treated.

Another area in need of an objective device and method for characterization of soft tissue is in detection of pelvic organ prolapse, a major cause of female incontinence. Pelvic organ prolapse (POP) is a highly prevalent condition affecting at least 50% of women in the US at some point during their lifetimes. One recent study including 27,342 women revealed that 40% percent of women aged 50 to 79 years have some form of pelvic organ prolapse. Some loss of utero-vaginal support occurs in most adult women. However, the true etiology of prolapse and differences seen among individuals are not entirely understood. Changes in the elasticity of the vaginal walls, connective support tissues, and muscles are thought to be significant factors in the development of pelvic organ prolapse. The high incidence of POP dictates the need for effective means of its early detection and characterization as well as evaluating the risk of further prolapse development.

Aspiration methods for assessment of elasticity of skin and other soft tissues are generally known. Typically, a device forms a cavity over a tissue sample. Air is then aspirated causing the tissue to be drawn into the cavity. Extent of tissue prolapse into the cavity is measured by various mechanical, optical or other means. Tissue elasticity is then determined based on the degree of such prolapse and the level of vacuum achieved by the device. Examples of prior art attempts at various devices based on this aspiration method are found in U.S. Pat. Nos. 4,365,638; 4,976,272; 5,278,776; 7,556,605; US Patent Application Publication No. 2008/0234607 and the PCT Publication No. WO 03/105689. These devices however lack the ability for a comprehensive assessment of tissue which goes beyond simple elasticity measurements.

Other areas of interest for detection of tissue elasticity include intraoperative detection of lesion boundaries during open surgery procedures.

The need therefore exists for improved methods and devices to measure various viscoelastic properties of soft tissues such as elasticity modulus, tissue viscosity and tissue creep.

SUMMARY OF INVENTION

Accordingly, it is an object of the present invention to overcome these and other drawbacks of the prior art by providing novel methods and devices for objective evaluation of viscoelastic properties of soft tissues.

It is another object of the invention to provide an aspiration method for objective evaluation of viscoelastic properties of soft tissues allowing for comprehensive tissue evaluation beyond determination of tissue elasticity by Young's modulus. Other properties of interest that can be determined using the method of the invention include tissue viscosity and tissue creep.

A novel aspiration method for measuring soft tissue mechanical properties uses a probe having a cavity with an outer edge adapted to sealingly come in contact with the tissue test area. A small diameter tube enters the cavity in its center and extends inside thereof to end at a specific distance from the plane defined by the outer edge of the cavity. A vacuum pump and pressure sensor are connected to other end of the tube. The vacuum pump is activated to aspirate air from the cavity placed over the tissue test area. This draws tissue inside the probe cavity. The aspiration rate is constant creating a linear relationship between the negative pressure inside the probe cavity and time. The domed tissue keeps moving into the cavity until it finally reaches the inner tube and closes its opening. At this point, the remaining cavity volume is isolated from the pump, the drop in pressure inside the cavity is stopped and the tissue remains in the same position despite continuous draw of the vacuum pump. The small volume inside the tube is the only volume exposed to continuing aspiration. An abrupt change in volume under continuing vacuum is detected by the pressure sensor as an abrupt change in slope of continuous pressure drop. The device monitors negative pressure in the probe to identify the inflection point in its slope indicating the touching of the end of the tube by the tissue. The Young's modulus is then calculated based for example on a predetermined calibration data and displayed on a screen. Performing successive measurements with different rates of air aspiration and with variable intervals between successive measurements allows determination of other rheological characteristics of tissue such as viscosity and shear creep.

The aspiration method of the invention comprising the steps of:
  a. providing a test cavity in a sealed contact with the tissue, the test cavity includes an opening connected to an aspiration system, b. activating the aspiration system to evacuate air from the cavity at a first rate of aspiration,
c. conducting pressure measurements in the test cavity as a function of time,
d. detecting a first slope of the pressure measurements in the test cavity,
e. detecting a first inflection point in the pressure measurements defining a first pressure level and a first time point at which the pressure measurements deviate from the first slope indicating closure of the opening by the tissue being drawn into the test cavity, the first inflection point is detected using one of methods selected as follows:
  i. detecting deviation of the first slope above a predetermined slope deviation threshold,
  ii. detecting a first derivative of said first slope exceeding a predetermined first derivative threshold, and
  iii. detecting a second derivative of said first slope exceeding a predetermined second derivative threshold,
f. determining elasticity of the tissue using the first pressure level.

Additional steps allow detecting other tissue parameters like viscosity and creep from repeated test measurements conducted at different rates of aspiration and with different waiting periods between the tests.

BRIEF DESCRIPTION OF THE DRAWINGS

A more complete appreciation of the subject matter of the present invention and the various advantages thereof can be realized by reference to the following detailed description in which reference is made to the accompanying drawings in which.

DETAILED DESCRIPTION OF THE INVENTION

Figure 1:
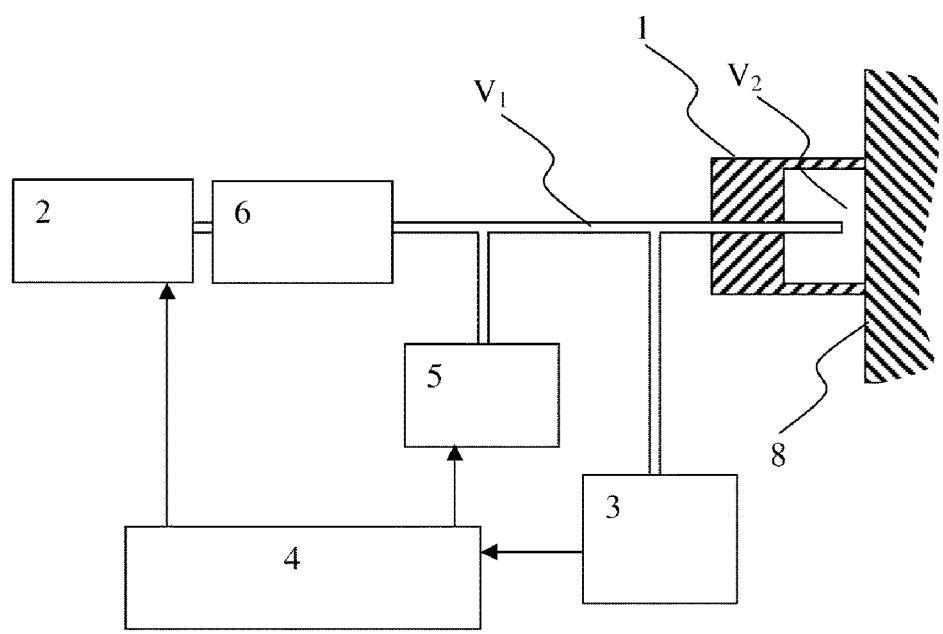
FIG. 1 is a block-diagram of the system of present invention.

A detailed description of the present invention follows with reference to accompanying drawings in which like elements are indicated by like reference letters and numerals. FIG. 1 illustrates a block diagram of the device of the invention. Arrows indicate electrical connections, while double lines indicate pneumatic connections. The device consists primarily of four basic components: a specially designed probe tip 1, a vacuum pump 2, a pressure sensor 3, and an electronic unit 4 for data acquisition, calculation and displaying the measurement results. An optional vent valve 5 is used to quickly release vacuum from the measuring cavity of the probe: it is closed when the measurement starts, and is opened to vent the cavity to atmosphere when the measurement is complete. A capillary restrictor 6 can be used for adjusting the rate of aspiration. The combined internal volume of all internal connection tubes, primarily internal volume 14 of tube 10 is assigned a value $V_1$. The open end cavity of the probe tip is placed on the tissue test area 8 to seal the volume $V_2$ inside the probe test cavity.

Pumping speed S defines aspiration rate of the cavity, governed by vacuum pump 2 and restrictor 6 properties, which in turn defines dependence of pressure P versus time t. For a pumped volume V in an air-tight system, the pressure change is described by the following general equation:

$$dP = -\frac{S}{V}Pdt$$

For small pressure changes, the value S may be considered a constant, so that $$P(t) = P_0 e^{-\frac{S}{V}(t-t_0)} \text{ or } P(t) = P_0\left(1 - \frac{S}{V}(t-t_0)\right) \text{ when } V \gg S_{(t-t_0)}.$$

These equations indicate that a large aspiration volume V will result in a lower slope of pressure change, while a higher pumping speed S will result in a higher slope of pressure change inside the probe cavity.

Figure 2A:
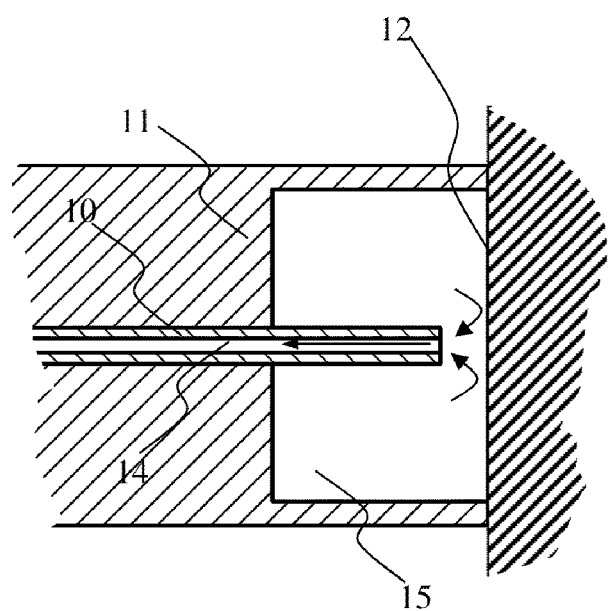
FIG. 2A is an enlarged cross-sectional side view of a probe cavity at the start of measurement procedure.
Figure 2B:
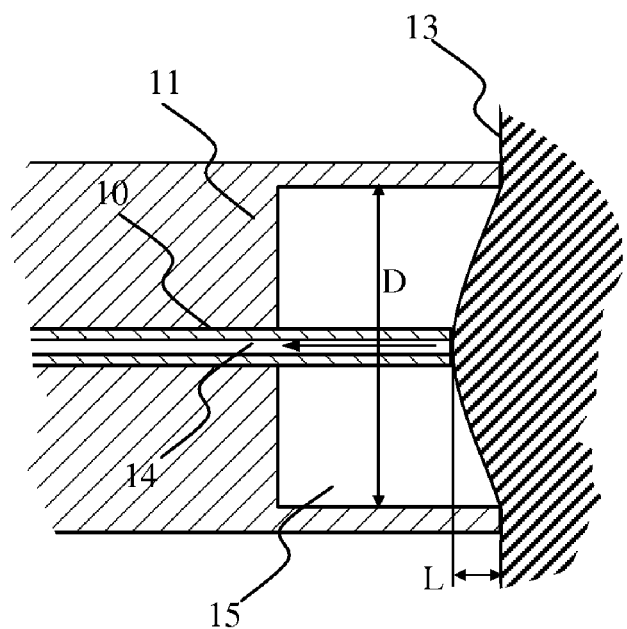
FIG. 2B is an enlarged cross-sectional side view of a probe cavity at the end of measurement procedure.
Figure 3:
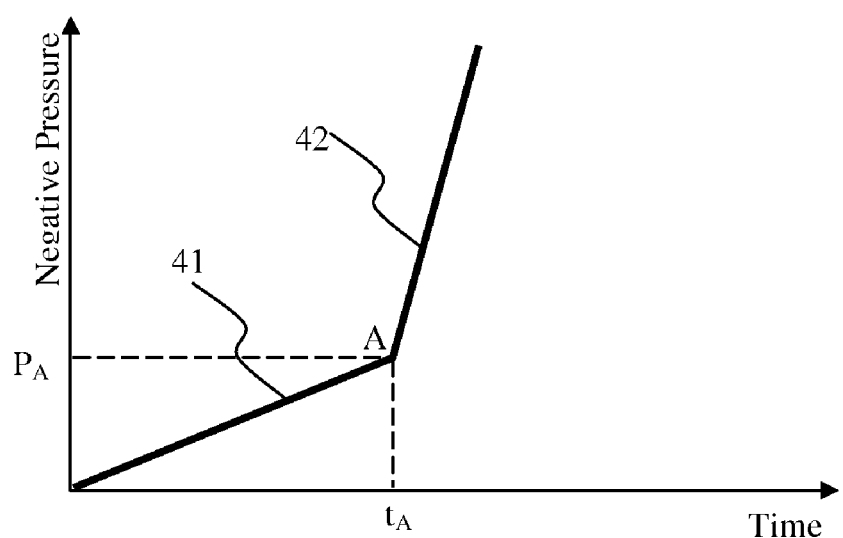
FIG. 3 is a typical pressure-time plot.

The basic principle behind the aspiration method of the invention is illustrated in FIG. 2. Cross-section of the probe cavity is shown here at the time when the measurement commences (FIG. 2A) and at the time when the tissue reaches the end of the tube causing an inflection point in the time-pressure plot (FIG. 2B). The small diameter tube 10 passes through the probe tip 11. To begin the test procedure, the probe cavity is placed in contact with the tissue test area 12, thereby creating a closed space 15 with volume $V_2$ between probe tip cavity and tissue 8. When the measurement is initiated, the vacuum pump 2 creates negative pressure in this closed space. This in turn draws the tissue towards the center of cavity. At this time, the speed S at which the negative pressure is created is constant and the total volume being aspirated is defined by the sum of volume $V_1$ of internal space 14 of tube 10 and volume $V_2$ of the closed space 15 ($V=V_1+V_2$). The time dependence of negative pressure $P_v=P_0-P(t)$ at this point is shown in FIG. 3 as line 41 that can be described by the following equation:

$$P_v = P_0 \frac{S}{V_1 + V_2} t \qquad (1)$$

The arrows in FIG. 2A show evacuated air going through the tube 10 leaving cavity space 15. The domed tissue 13 keeps extending inside the cavity until it finally touches the small diameter inner tube. At this point (shown in FIG. 2B), the volume $V_2$ of space 15 is isolated from the pump 2 and tube 10, and as a result the rate at which negative pressure is created changes depending on the internal volume 14 of tube 10. The arrow in FIG. 2B shows that air is aspirated just from volume $V_1$ of tube 10. Time dependence of negative pressure at this time is shown in FIG. 3 as line 42 described by the following equation:

$$P_v = P_A + P_0 \frac{S}{V_1}(t - t_A) \quad (2)$$

Importantly, the pressure-time plot changes slope at inflection point A in FIG. 3. The higher the difference between $V_1+V_2$ and $V_1$, the sharper the bending of curve will be at inflection point A.

Figure 4:
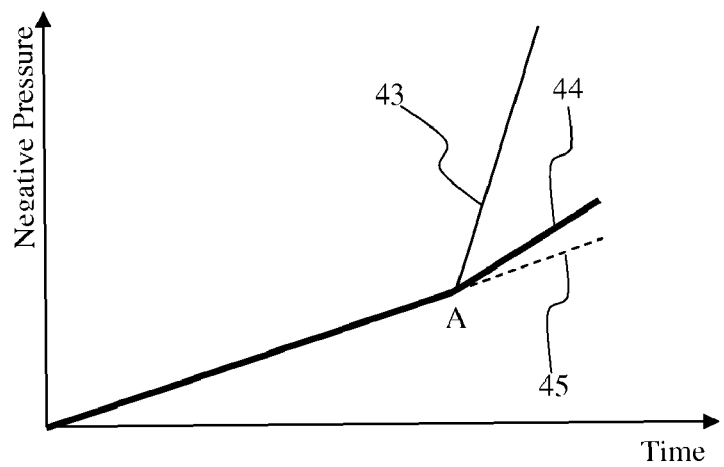
FIG. 4 is a pressure-time plot for different ratios of cavity volume to tube volume.
Figure 5:
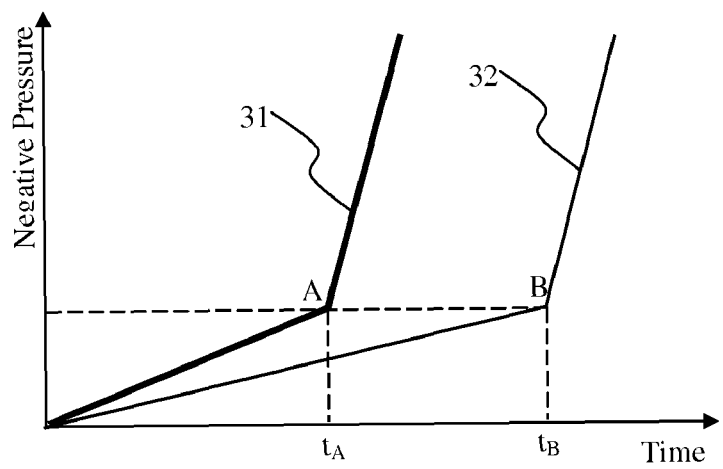
FIG. 5 is a pressure-time plot for probe cavities with different volume.
Figure 6:
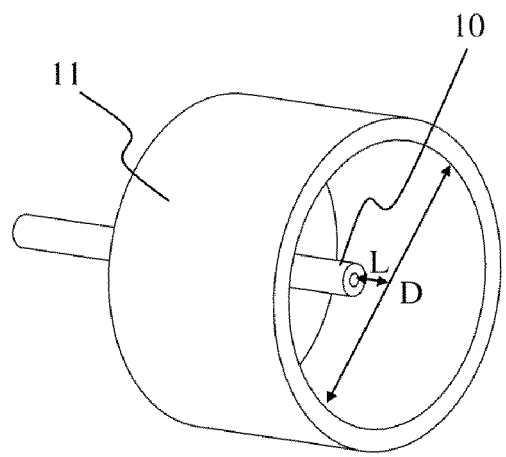
FIG. 6 is an elevation view of a general purpose probe tip.

FIG. 4 illustrates how the ratio of volumes $V_1$ and $V_2$ characterize the bend in pressure curve. With the same total volume $V_1+V_2$, curve 43 shows the bend when $9V_1=V_2$, curve 44 shows the bend when $V_1=V_2$, and curve 45 shows the bend when $V_1=9V_2$. This figure illustrates that the finding of inflection point is easier (with a smaller error) when volume $V_1$ of tube 14 is considerably smaller then internal cavity volume $V_2$. For practical purposes, the ratio of cavity volume to the volume of tube 10 is selected to be between 2 and 10. Higher than 10 ratios do not considerably improve measurement accuracy but cause an undesirable increase in test duration. FIG. 5 illustrates how the negative pressure changes in time for different probe tips. Activation of the vacuum pump 2 creates a negative pressure inside the probe cavity and the pressure-time plot shows a closely linear characteristic in accordance with equation (1). For a given volume $V_1$ of tube 10, the larger the volume $V_2$ of the probe cavity, the smaller is the slope of this line. Curve 31 (thicker line) illustrates a pressure-time plot for a probe tip with a smaller volume $V_2$ as compared with the curve 32.

Figure 7:
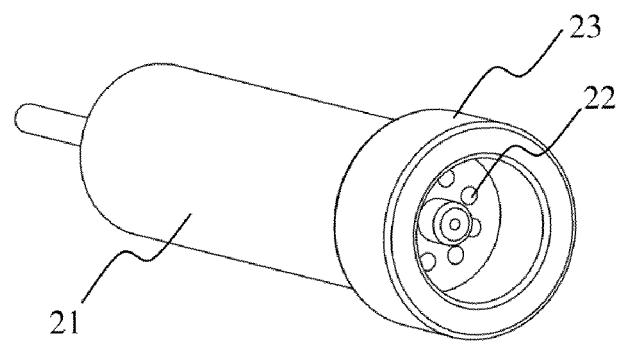
FIG. 7 is an elevation view of a probe tip with small diameter.
Figure 8:
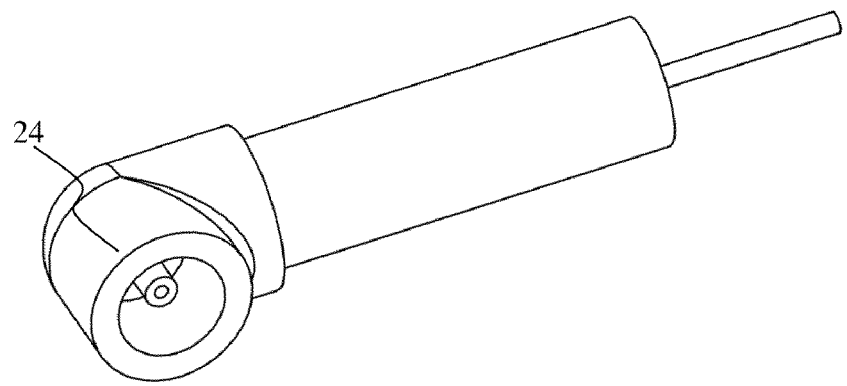
FIG. 8 is an elevation view of a right-angled probe tip.
Figure 9:
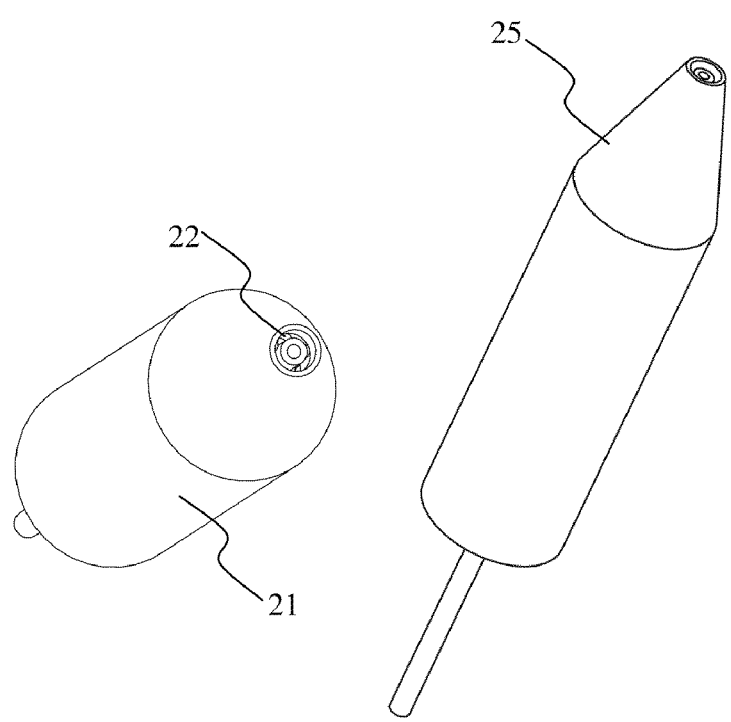
FIG. 9 is an elevation view of a miniature probe tip.

Different kinds of probe tips are shown in FIGS. 6 through 9. One advantage of the device of the invention is that the tip containing the test cavity may have provisions allowing it to detach from the probe. This in turn allows the replaceable tip to be optionally disposable so as to avoid the need for sterilization of the entire probe between patient examinations. The simplest (see FIG. 6) is a general purpose tip. It consists of a small diameter tube 10 inside the probe tip 11, which is a hollow cylinder with an open end. The diameter D of this cylinder characterizes the area the probe that covers the tested tissue. Tube 10 is placed in the center of the cylinder and ends at a specific distance L from the open end plane (refer to cross-section shown in FIG. 2). For applications where the tissue sample has only a small test area available for evaluation, a probe tip with smaller tip diameter is required. Such a probe is shown in FIG. 7. It is similar to the general purpose tip with the exception of structural tube holder 21 that provides access to tissue at a distance. To produce a sharp inflection point, the internal space of the structural tube holder 21 can be connected to the internal space of probe head 23 through holes 22. For difficult to reach applications, a right angled probe tip 24 can be used as shown in FIG. 8. Subminiature probe tips are shown in FIG. 9. A distinctive feature of this tip is a miniature tip diameter D, as compared to other tips. Internal space of structural tube holder 21 is used to provide additional aspiration volume. A conical head 25 provides transition to the small diameter opening of the probe.

The probe tip diameter D and distance L between the open end plane of this tip and tube with small diameter (see FIG. 6) define the pressure required to reach an inflection point for a sample tissue with elasticity module E. Thus values D, L and range of measured pressures should be optimized to reach acceptable accuracy for specific measuring range of values E. The test time depends on the volume of the probe and aspiration rate of the vacuum pump 2 (with capillary restrictor 6, if used). It should be optimized to reach acceptable accuracy of measurement in a reasonable time. Using probe tips with different values D and L provides an opportunity to examine the elasticity modulus of different biological tissues (skin, muscles, vessels), as well as non-biological soft materials (silicones, gels etc.).

Figure 10:
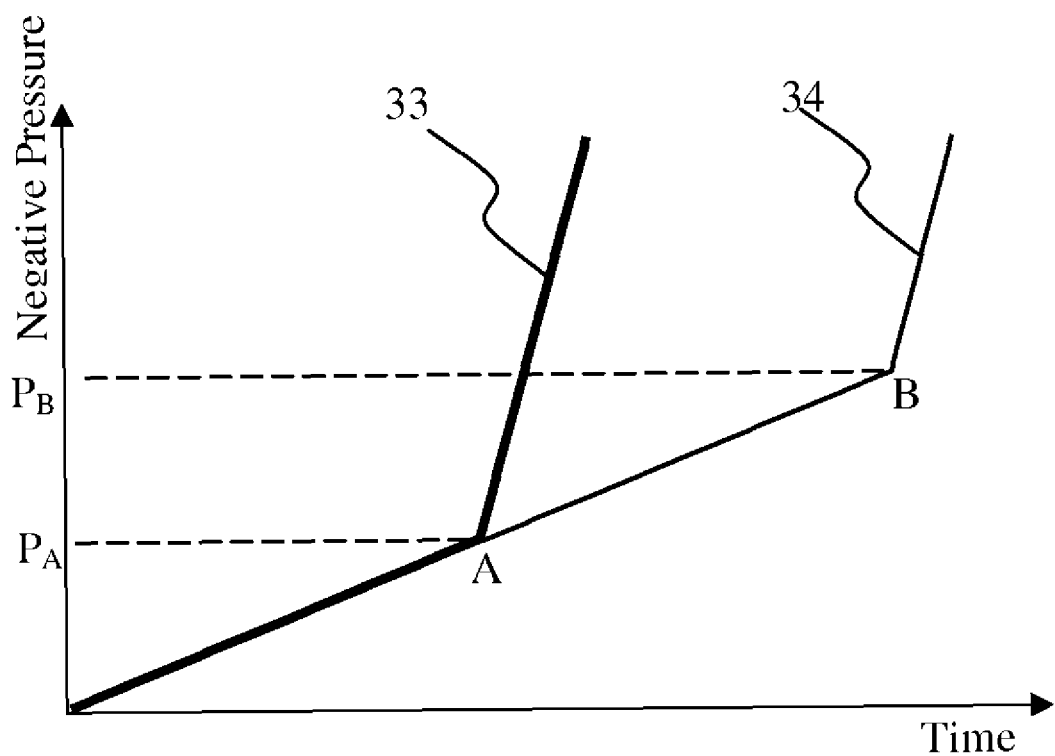
FIG. 10 is a pressure-time plot for tissue samples with different elasticity Young's modulus.

FIG. 10 illustrates how the pressure in the cavity changes with respect to aspiration time for samples with different mechanical properties. The softer the tissue, the sooner the inflection point is reached on the pressure plot. The tissue with inflection point A (thick curve 33, FIG. 10) is softer then tissue with inflection point B (thin curve 34, FIG. 10), because $P_A<P_B$. Based on this dependence, device can be programmed to determine elasticity modulus as a function of the pressure level at the inflection.

Figure 11:
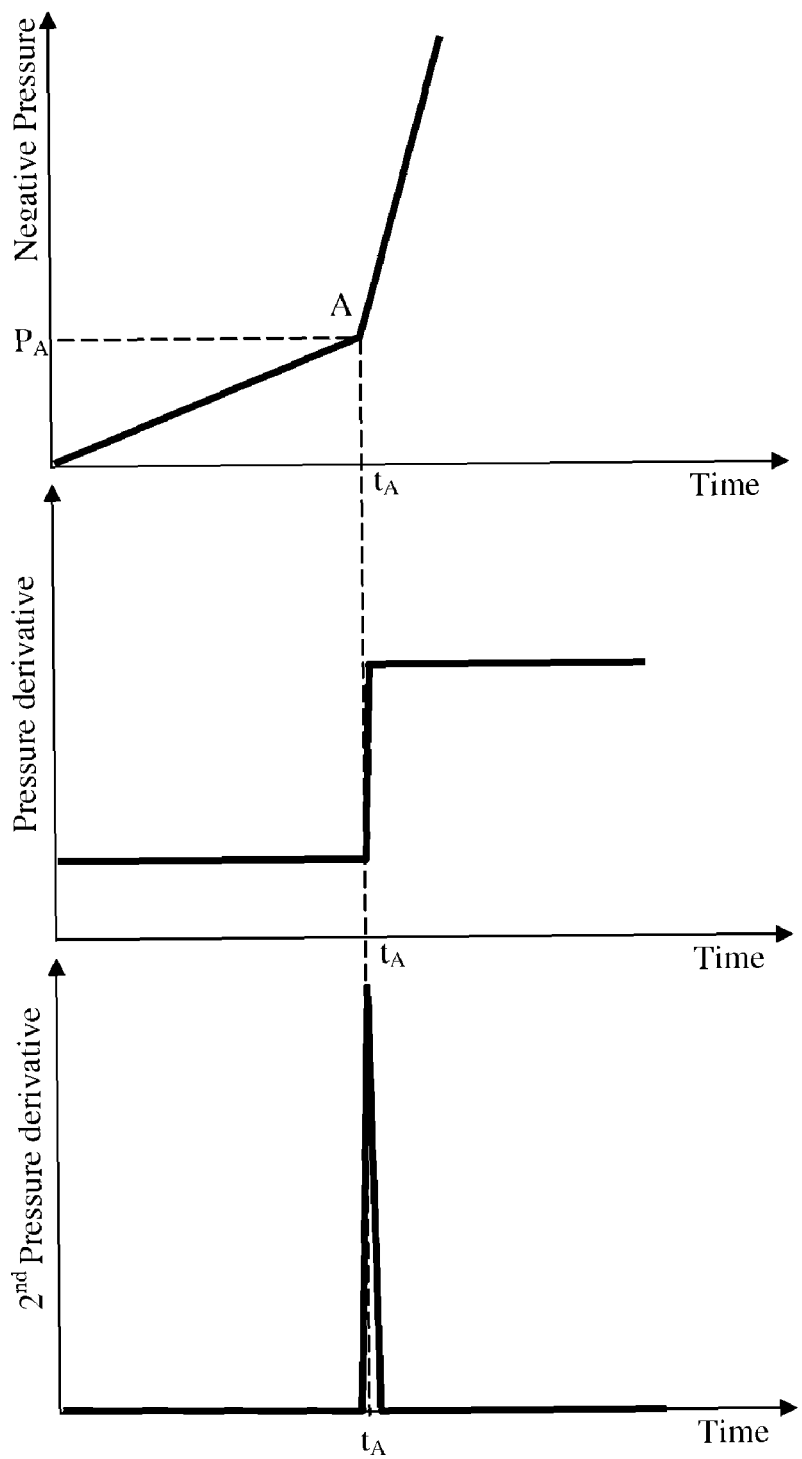
FIG. 11 is a pressure-time plot with its first derivative and its second derivative.

FIG. 11 illustrates different methods of finding the inflection point and a corresponding pressure level. One method is to identify the inflection point on the pressure-time plot as a sharp bend (point A). This can be done when the pressure measurements deviate from the detected slope by more than a predetermined threshold. The threshold is selected to avoid false positives caused by measurement noise. A second method is to detect the inflection point when a first derivative of the pressure plot exceeds a predetermined first derivative threshold level, which is selected above the measurements noise level. And lastly, the inflection pressure point can be detected as a point at which the second derivative of the pressure plot peaks above a predetermined second derivative threshold level, which is selected to be above the noise level of measurements.

Figure 12:
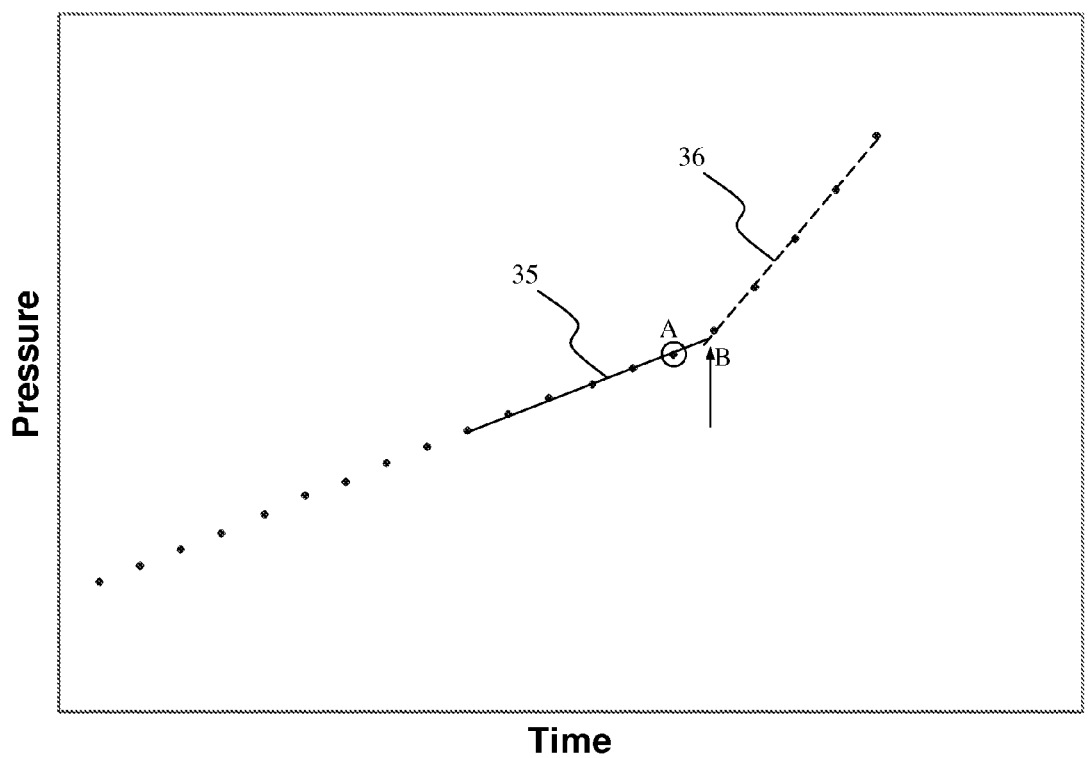
FIG. 12 illustrates the characteristic pressure inflection point calculation procedure.

Practical pressure sensor readings may represent a number of distinct individual measurements at a certain sampling frequency rather than a continuous curve as shown in FIG. 12. Detecting an inflection point may be difficult as it can fall in between individual pressure measurements. In this case, a preliminary inflection point A, circled in the figure, can be found using one of the above mentioned methods. The final inflection point B is then corrected and defined as the intersection of a best-fit straight line 35 (solid line) through pressure measurements prior to point A and a best-fit straight line 36 (dashed line) through the pressure measurements after point A on the pressure-time plot. In this example, the corrected inflection point falls between the pressure measurement points. The arrow in FIG. 10 indicates the corrected more accurate inflection point.

One advantageous way to change the aspiration rate from the measuring cavity is to change the speed of vacuum pump 2, preferably in known increments defining various known aspiration rates.

Figure 13:
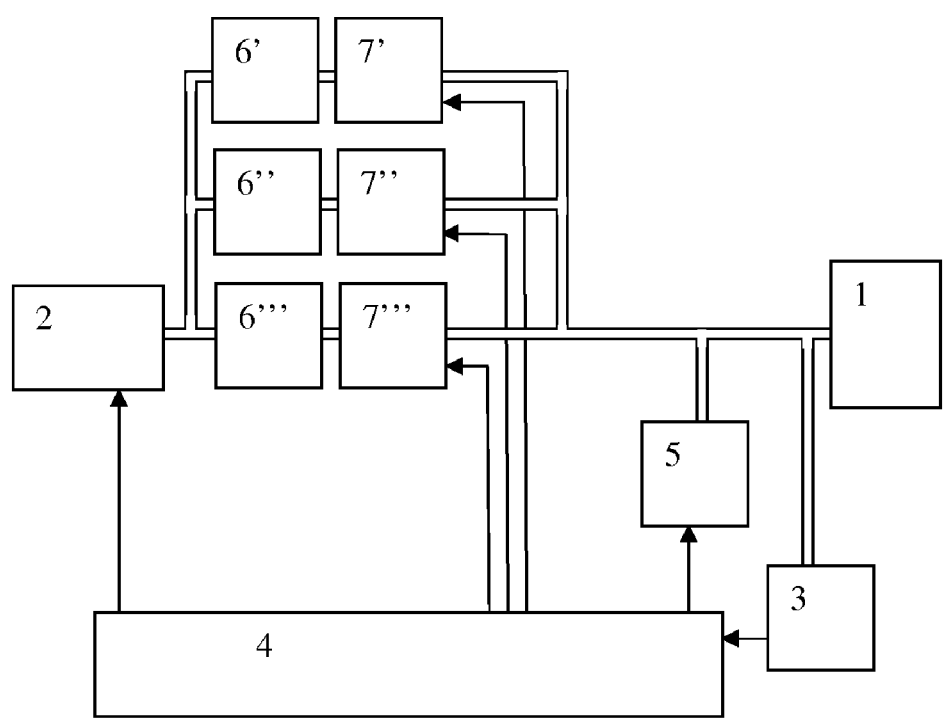
FIG. 13 is a block-diagram of an advanced system of present invention having multiple aspiration tubes.

FIG. 13 illustrates another alternate way to adjust the rate of aspiration in a block-diagram of a more advanced device than the one shown in FIG. 1. This device allows measurement of tissue viscosity and shear creep in addition to tissue elasticity. This is achieved by providing an ability to create negative pressure in the test cavity at different rates of aspiration. Main elements of this device are the same as described above but instead of one capillary restrictor 6, there is provided a set of several (three in this case) parallel restrictors 6', 6", and 6'" connected through corresponding shut-off valves 7', 7", and 7'" to the vacuum pump 2. Each capillary restrictor optionally has a different diameter and as a result different resistance to air flow therethrough. A set of three restrictor valves provides a total of seven different possible speeds of aspiration depending on the opening of one, two or three valves 7. The electronic unit drives the pump 2 and valves 7 and monitors the pressure sensor readings based on the pressure inside the probe cavity. Vent valve 5 is used to quickly release vacuum from the probe when the test is over.

Figure 14A:
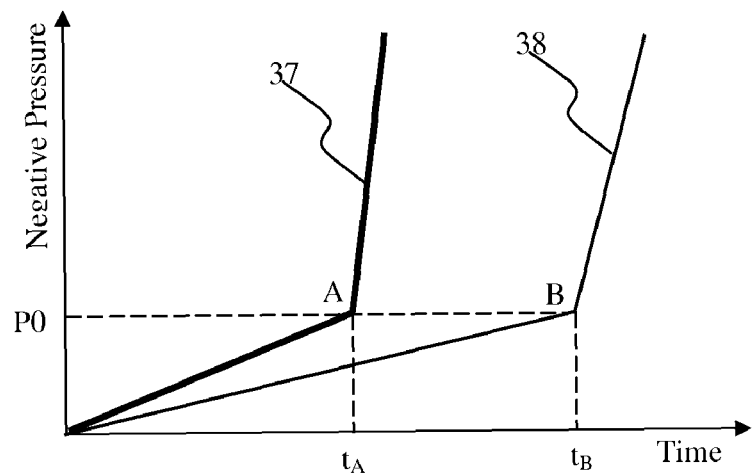
FIGS. 14A and 14B are pressure-time plots for different aspiration speeds allowing assessment of tissue viscosity.

The method of evaluation of tissue viscosity according to the invention is based on dependence between the rate of aspiration and inflection point. For a non-viscous media or low viscosity tissue, the inflection point does not change with various aspiration speeds. The pressure-time plot in FIG. 14A shows the influence of different aspiration rates on inflection point. Thick curve 37 with inflection point A illustrates faster aspiration rate than thin curve 38 with inflection point B ($t_A<t_B$, thin curve has larger slope), while the inflection pressure is the same ($P0=P_A=P_B$). According to the method of the invention, the test is first conducted with a first rate of aspiration and then with a second rate of aspiration. A first waiting period is included between the first and a second measurement to allow the tissue to relax completely to its initial state.

Figure 14B:
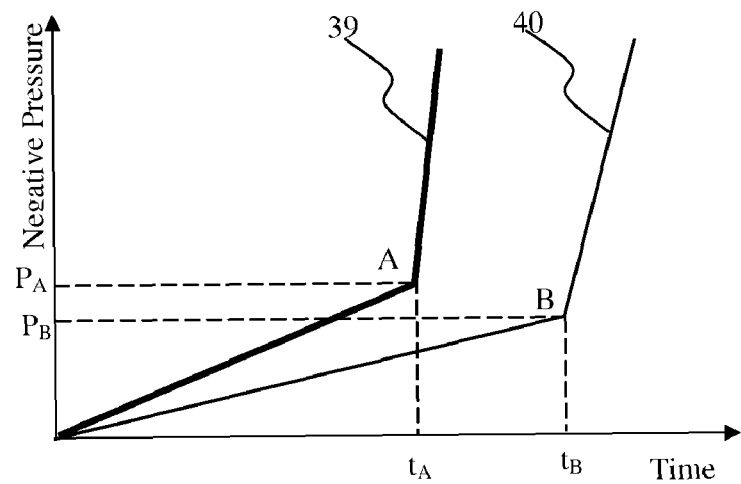

The pressure-time plot in FIG. 14B shows the influence of aspiration rates on inflection pressure for a tissue sample having higher tissue viscosity. Thick curve 39 with inflection point A illustrates faster aspiration rate then thin curve 40 with inflection point B ($t_A<t_B$, thin curve has larger slope). Because vacuum should be applied longer to overcome tissue sample's resistance for motion (viscosity), the inflection pressure for fast aspiration rate is higher ($P_A>P_B$). The device can be calibrated with samples of known viscosity to evaluate functional dependence of tissue viscosity on pressure difference $dP0=P_A-P_B$ for a specific change in aspiration rate. The accuracy of viscosity evaluation can be improved by testing different aspiration rates and choosing the optimal difference. Once calibration is obtained, tissue testing can be accomplished by repeating aspiration procedures at different aspiration rates.

Figure 15A:
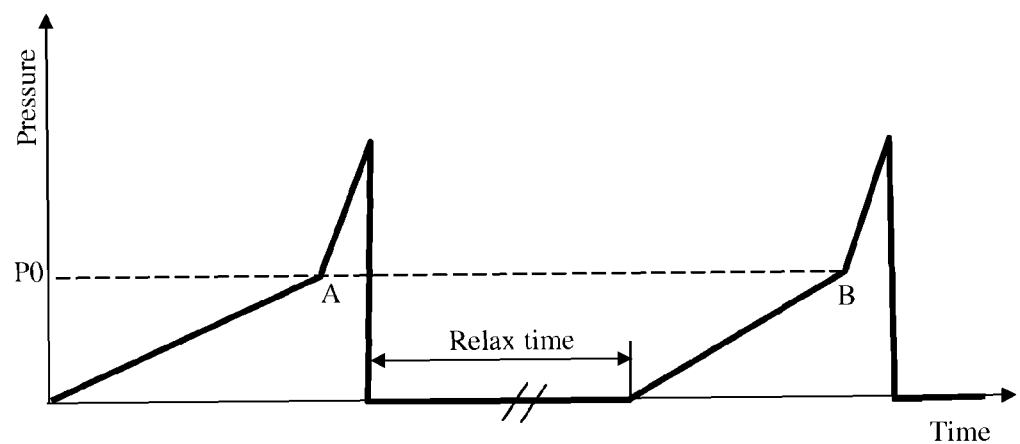
FIGS. 15A and 15B are pressure-time plots developed for assessment of tissue shear creep.
Figure 15B:
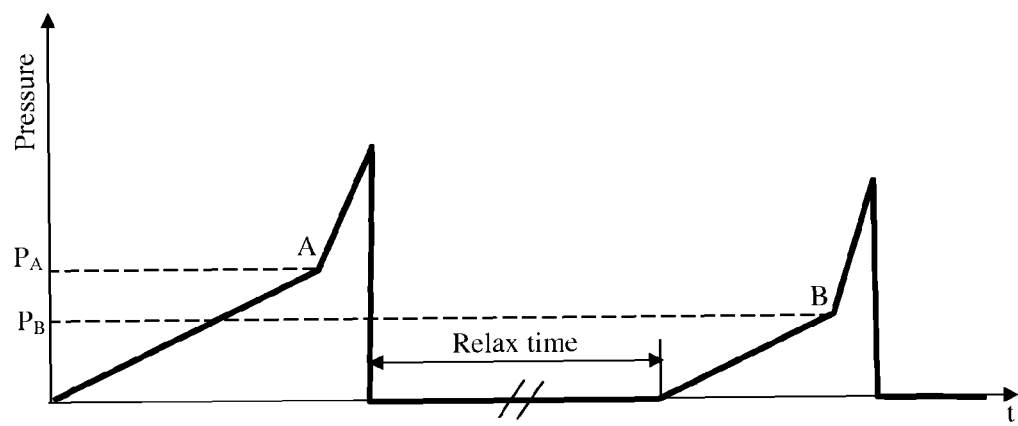

The method of evaluation of tissue creep is based on identifying the change in inflection point pressure when the test is repeated for a second time after a predetermined relax time period. For a low creep tissue sample, the inflection pressure $P_0$ stays the same when the test is repeated again, as shown in FIG. 15A. FIG. 15B illustrates a pressure-time plot of repeated tests for a sample having higher tissue creep. Each successive test results in a lower inflection pressure due to residual deformation of tissue remaining from a previous test ($P_A>P_B$). The device can be calibrated with known samples to evaluate functional dependence of tissue creep on pressure difference. The accuracy of creep evaluation can be improved by optimization of a relax time period. Properly selected relax time period for measuring tissue creep does not necessarily allow it to get back to its original condition so as to detect the difference between the first and the second measurement.

In case both the tissue elasticity and tissue creep are measured, the test can be repeated at least three times with variable rates of aspiration and waiting times between the tests.

Figure 16:
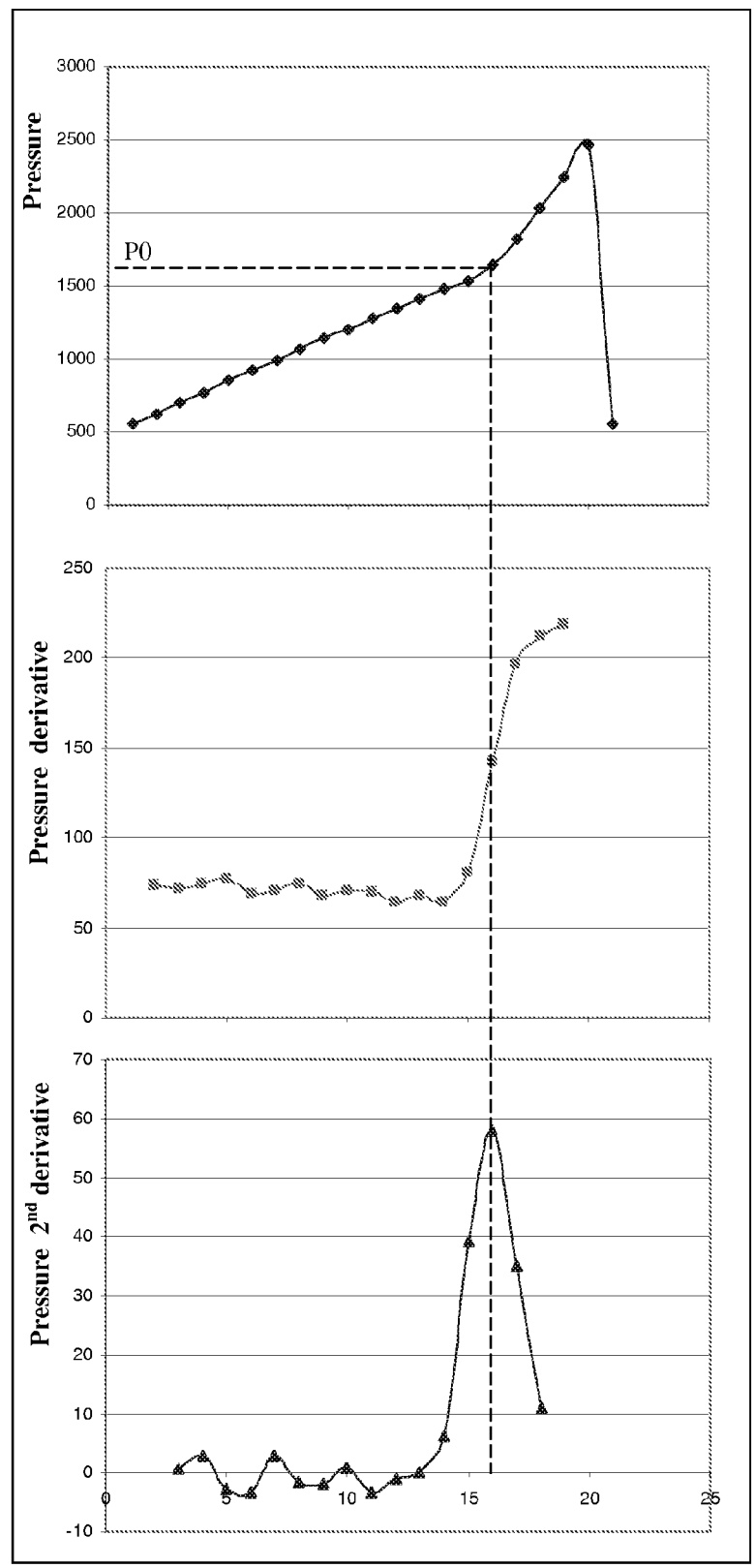
FIG. 16 is an example of a recorded pressure plot, its first derivative and second derivative.
Figure 17:
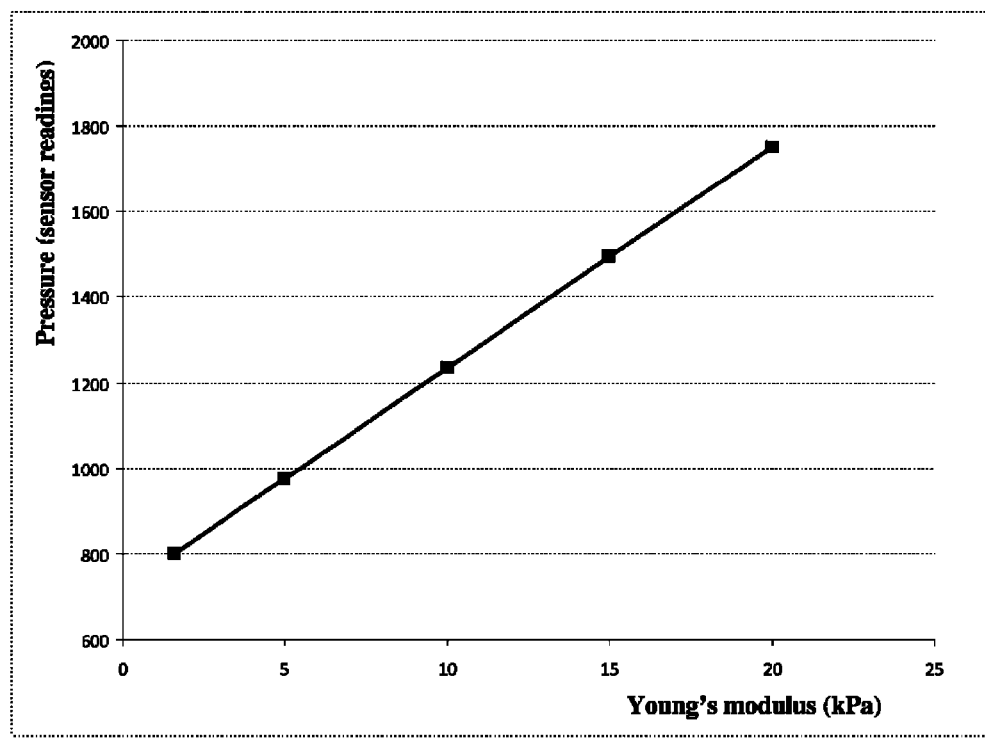
FIG. 17 is an example of device calibration curve with a range of elasticity moduli.

The above mentioned principles were implemented in a device that monitors negative pressure inside the tip cavity, identifies the point of abrupt change in pressure defining an inflection point that depends on mechanical properties of the sample, calculates the Young's modulus based on programmed calibration and displays this value on LCD. Examples of a pressure sensor reading together with its first and second derivatives obtained by this device are shown in FIG. 16. An example of a calibration curve for certain range of tissue elasticity is shown in FIG. 17. The curve demonstrates close-to-linear dependence between pressure and elasticity modulus.

In all of the above methods of evaluation of tissue viscoelastic properties, the presence of the inflection point is continuously monitored and once detected, the test is stopped and the cavity is immediately vented to release the test tissue and avoid its bruising from continuous exposure to vacuum.

Although the invention herein has been described with respect to particular embodiments, it is understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

What is claimed is:

1. An aspiration method for assessing viscoelastic properties of soft tissue, the method comprising the steps of:
    a) providing a test cavity in a sealed contact with said tissue, said test cavity includes an opening connected to an aspiration system, said opening located on a path of expected deformation of said tissue,
    b) activating said aspiration system to evacuate air through said opening from said cavity at a first rate of aspiration to draw said tissue into said cavity,
    c) conducting pressure measurements in said aspiration system and said test cavity as a function of time as said tissue is being drawn into said cavity, continue to draw said tissue into said cavity to cause closure of said opening by said tissue and separation of said test cavity from said aspiration system,
    d) detecting a first slope of said pressure measurements in said test cavity,
    e) detecting a first inflection point in said pressure measurements, said first inflection point defining a first pressure level and a first time point at which said pressure measurements deviate from said first slope indicating closure of said opening by said tissue and cessation of said tissue being drawn into said test cavity, said first inflection point is detected using a method selected from a group consisting of:
        i. detecting deviation of said first slope above a predetermined slope deviation threshold,
        ii. detecting a first derivative of said first slope exceeding a predetermined first derivative threshold, and
        iii. detecting a second derivative of said first slope exceeding a predetermined second derivative threshold,
    f) determining elasticity of said tissue using said first slope of said pressure measurements and said first pressure level at said first inflection point.

2. The method as in claim 1, wherein said step (d) further including constructing a first best-fit straight line through said measurements located prior to said inflection point and a second best-fit straight line through said measurements located after said inflection point, said method further including defining a corrected inflection point located at an intersection of said first best-fit straight line and said second best-fit straight line.

3. The method as in claim 1, wherein said test is stopped once said inflection point is determined and said cavity is immediately vented to release said tissue.

4. The method as in claim 1 further comprising venting said cavity to release said tissue, waiting during a first predetermined time to allow said tissue to relax, and repeating steps (b) through (f) wherein step (b) includes evacuating air from said cavity at a second rate of aspiration, said step (d) includes detecting a second slope of pressure measurements in said cavity, said step (e) includes detecting a second inflection point defining a second pressure level and a second time point at which said tissue is drawn into said test cavity, said step (f) further including determining tissue viscosity using said first pressure level and said second pressure level.

5. The method as in claim 1, further comprising the steps of:
   g. venting said cavity to release said tissue,
   h. waiting during a second predetermined time to allow said tissue to partially relax, and
   i. repeating steps (b) through (g) to detect a third inflection point defining a third pressure level,
   wherein said step (f) further including determining tissue creep using said first pressure level and said third pressure level.

6. The method as in claim 1, wherein in step (e) said first slope increases in value after said first pressure level and said first time point.

* * * * *